(12) United States Patent
Capelli et al.

(10) Patent No.: US 7,863,299 B2
(45) Date of Patent: *Jan. 4, 2011

(54) TRIAZOLYL DERIVATIVES OF AZABICYCLO [3.1.0] HEXANE AS DOPAMINE D3 RECEPTOR MODULATORS

(75) Inventors: Anna Maria Capelli, Verona (IT); Elettra Fazzolari, Verona (IT); Fabrizio Micheli, Verona (IT); Giovanna Tedesco, Verona (IT); Silvia Terreni, Verona (IT)

(73) Assignee: Glaxo Group Limited, Middlesex (GB)

( * ) Notice: Subject to any disclaimer, the term of this patent is extended or adjusted under 35 U.S.C. 154(b) by 0 days.

This patent is subject to a terminal disclaimer.

(21) Appl. No.: 12/064,118

(22) PCT Filed: Aug. 18, 2006

(86) PCT No.: PCT/EP2006/008203

§ 371 (c)(1),
(2), (4) Date: Feb. 19, 2008

(87) PCT Pub. No.: WO2007/022936

PCT Pub. Date: Mar. 1, 2007

(65) Prior Publication Data

US 2008/0242715 A1 Oct. 2, 2008

(30) Foreign Application Priority Data

Aug. 22, 2005 (GB) .................................. 0517187.1

(51) Int. Cl.
*A61K 31/428* (2006.01)
*A61K 31/4196* (2006.01)
*A61K 31/4439* (2006.01)
*C07D 403/14* (2006.01)
*C07D 417/14* (2006.01)

(52) U.S. Cl. ..................... 514/341; 546/272.4; 548/152; 548/263.2

(58) Field of Classification Search .................. 514/341; 546/272.4; 548/263.2
See application file for complete search history.

(56) References Cited

U.S. PATENT DOCUMENTS 6,204,284 B1   3/2001  Beer et al.
2007/0142438 A1* 6/2007 Arista et al. ................. 514/341

FOREIGN PATENT DOCUMENTS

WO   WO02/040471       5/2002
WO   WO 2005/080382 A1 * 1/2005
WO   WO2005/080382     9/2005
WO   WO2006/108700    10/2006

(Continued)

OTHER PUBLICATIONS

Patini et al, Chem. Rev., 1996, 96(8), pp. 3147-3176, esp. p. 3150.*

(Continued)

*Primary Examiner*—Susannah Chung
(74) *Attorney, Agent, or Firm*—James M. Kanagy; Edward R. Gimmi; Charles M. Kinzig

(57) ABSTRACT

The present invention relates to novel compounds of formula (IC) or a salt thereof:

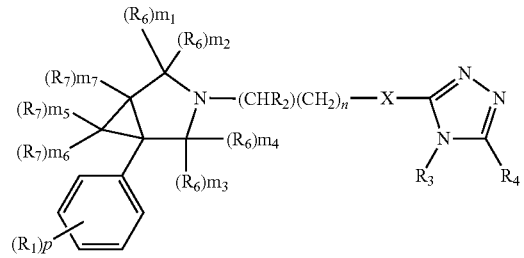

(IC)

wherein:
p is an integer ranging from 0 to 4;
$R_1$ is independently selected from a group consisting of: halogen, hydroxy, cyano, $C_{1-4}$alkyl, halo$C_{1-4}$alkyl, $C_{1-4}$alkoxy, halo$C_{1-4}$alkoxy, $C_{1-4}$alkanoyl or $SF_5$; or corresponds to a group $R_5$;
$m_1$, $m_2$, $m_3$, and $m_4$ are 0;
$m_5$, $m_6$ and $m_7$ are each independently 0, 1 or 2 wherein the sum of $m_5$, $m_6$ and $m_7$ is 1 or 2;
$R_6$ is $C_{1-6}$alkyl;
$R_7$ is halogen, $C_{1-6}$alkyl or halo$C_{1-6}$alkyl;
$R_2$ is hydrogen or $C_{1-4}$alkyl;
n is 2 or 3;
X is S or —$CH_2$—;
$R_3$ is $C_{1-4}$alkyl;
$R_4$ is hydrogen, or a phenyl group, a heterocyclyl group, a 5- or 6-membered heteroaromatic group, or a 8- to 11-membered bicyclic group, any of which groups is optionally substituted by 1, 2, 3 or 4 substituents selected from the group consisting of: halogen, cyano, $C_{1-4}$alkyl, halo$C_{1-4}$alkyl, $C_{1-4}$alkoxy and $C_{1-4}$alkanoyl;
$R_5$ is isoxazolyl, —$CH_2$—N-pyrrolyl, 1,1-dioxido-2-isothiazolidinyl, thienyl, thiazolyl, pyridyl or 2-pyrrolidinonyl, wherein each group is optionally substituted by one or two substituents selected from: halogen, cyano, $C_{1-4}$alkyl, halo$C_{1-4}$alkyl, $C_{1-4}$alkoxy and $C_{1-4}$alkanoyl;
with the proviso that when $m_5=m_6=1$, $R_7$ is not chlorine;
processes for their preparation, intermediates used in these processes, pharmaceutical compositions containing them and their use in therapy, as modulators of dopamine $D_3$ receptors, e.g. to treat substance related disorders, as antipsychotic agents, premature ejaculation or cognition impairment.

12 Claims, No Drawings

U.S. PATENT DOCUMENTS

| | | | |
|---|---|---|---|
| 2007/0249642 A1 | 10/2007 | Bertani et al. | 514/269 |
| 2008/0058398 A1 | 3/2008 | Anderton et al. | 514/374 |
| 2008/0167357 A1 | 7/2008 | Hamprecht et al. | 514/384 |
| 2008/0176917 A1* | 7/2008 | Andreotti et al. | 514/384 |
| 2008/0227837 A1* | 9/2008 | Arista et al. | 514/384 |
| 2008/0242715 A1* | 10/2008 | Capelli et al. | 514/384 |
| 2009/0030062 A1 | 1/2009 | Gentile et al. | 514/412 |
| 2009/0036461 A1 | 2/2009 | Hamprecht et al. | 514/252.06 |
| 2009/0124629 A1 | 5/2009 | Bonanomi et al. | 514/252.06 |
| 2009/0221593 A1* | 9/2009 | Bonanomi et al. | 514/249 |
| 2009/0221618 A1 | 9/2009 | Arista et al. | 514/274 |

FOREIGN PATENT DOCUMENTS

| | | |
|---|---|---|
| WO | WO2006/108701 | 10/2006 |

OTHER PUBLICATIONS

U.S. Appl. No. 11/917,352, filed Jun. 13, 2006, Arista, et al.
U.S. Appl. No. 12/295,024, filed Mar. 30, 2007, Bertani, et al.
U.S. Appl. No. 12/295,304, filed Mar. 30, 2007, Bertani, et al.

* cited by examiner

TRIAZOLYL DERIVATIVES OF AZABICYCLO [3.1.0] HEXANE AS DOPAMINE D3 RECEPTOR MODULATORS

The present invention relates to novel compounds, processes for their preparation, intermediates used in these processes, pharmaceutical compositions containing them and their use in therapy, as modulators of dopamine $D_3$ receptors.

WO 2002/40471 (SmithKline Beecham) discloses certain benzazepine compounds having activity at the dopamine $D_3$ receptor.

Recently a patent application has been published as WO2005/080382 and discloses the following compounds of formula (I) or a salt thereof:

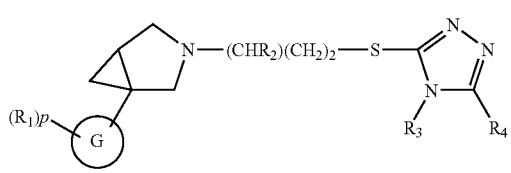

(I)

wherein
G is selected from a group consisting of: phenyl, pyridyl, benzothiazolyl, indazolyl;
p is an integer ranging from 0 to 5;
$R_1$ is independently selected from a group consisting of: halogen, hydroxy, cyano, $C_{1-4}$alkyl, halo$C_{1-4}$alkyl, $C_{1-4}$alkoxy, halo$C_{1-4}$alkoxy, $C_{1-4}$alkanoyl; or corresponds to a group $R_5$;
$R_2$ is hydrogen or $C_{1-4}$alkyl;
$R_3$ is $C_{1-4}$alkyl;
$R_4$ is hydrogen, or a phenyl group, a heterocyclyl group, a 5- or 6-membered heteroaromatic group, or a 8- to 11-membered bicyclic group, any of which groups is optionally substituted by 1, 2, 3 or 4 substituents selected from the group consisting of: halogen, cyano, $C_{1-4}$alkyl, halo$C_{1-4}$alkyl, $C_{1-4}$alkoxy, $C_{1-4}$alkanoyl;
$R_5$ is a moiety selected from the group consisting of: isoxazolyl, —CH₂—N-pyrrolyl, 1,1-dioxido-2-isothiazolidinyl, thienyl, thiazolyl, pyridyl, 2-pyrrolidinonyl, and such a group is optionally substituted by one or two substituents selected from: halogen, cyano, $C_{1-4}$alkyl, halo$C_{1-4}$alkyl, $C_{1-4}$alkoxy, $C_{1-4}$alkanoyl;

and when $R_1$ is chlorine and p is 1, such $R_1$ is not present in the ortho position with respect to the linking bond to the rest of the molecule; and when $R_1$ corresponds to $R_5$, p is 1.

A new class of compounds which have affinity for dopamine receptors, in particular the dopamine $D_3$ receptor has been found. These compounds have potential in the treatment of conditions wherein modulation, especially antagonism/inhibition, of the $D_3$ receptor is beneficial, e.g. to treat drug dependency or as antipsychotic agents.

The present invention provides a compound of formula (I) or a salt thereof:

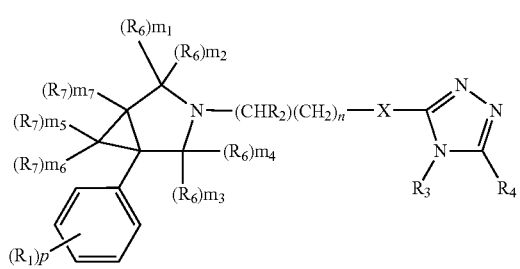

(I)

wherein:

p is an integer ranging from 0 to 4;

$R_1$ is independently selected from a group consisting of: halogen, hydroxy, cyano, $C_{1-4}$alkyl, halo$C_{1-4}$alkyl, $C_{1-4}$alkoxy, halo$C_{1-4}$alkoxy, $C_{1-4}$alkanoyl or $SF_5$; or corresponds to a group $R_5$;

$m_1$, $m_2$, $m_3$, $m_4$, $m_5$, $m_6$ and $m_7$ are each independently 0, 1 or 2 wherein the sum of $m_1$, $m_2$, $m_3$, $m_4$, $m_5$, $m_6$ and $m_7$ is 1 or 2;

$R_6$ is $C_{1-6}$alkyl;

$R_7$ is halogen, $C_{1-6}$alkyl or halo$C_{1-6}$alkyl;

$R_2$ is hydrogen or $C_{1-4}$alkyl;

n is 2 or 3;

X is S or —CH₂—;

$R_3$ is $C_{1-4}$alkyl;

$R_4$ is hydrogen, or a phenyl group, a heterocyclyl group, a 5- or 6-membered heteroaromatic group, or a 8- to 11-membered bicyclic group, any of which groups is optionally substituted by 1, 2, 3 or 4 substituents selected from the group consisting of: halogen, cyano, $C_{1-4}$alkyl, halo$C_{1-4}$alkyl, $C_{1-4}$alkoxy and $C_{1-4}$alkanoyl;

$R_5$ is isoxazolyl, —CH₂—N-pyrrolyl, 1,1-dioxido-2-isothiazolidinyl, thienyl, thiazolyl, pyridyl or 2-pyrrolidinonyl, wherein each group is optionally substituted by one or two substituents selected from: halogen, cyano, $C_{1-4}$alkyl, halo$C_{1-4}$alkyl, $C_{1-4}$alkoxy and $C_{1-4}$alkanoyl;

With the proviso that when m5=m6=1, $R_7$ is not chlorine.

In another embodiment, the present invention provides a compound of formula (IC) or a salt thereof:

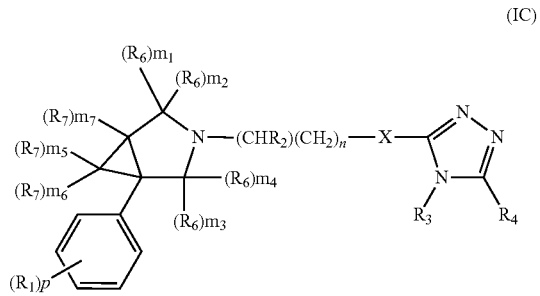

(IC)

wherein:

p is an integer ranging from 0 to 4;

$R_1$ is independently selected from a group consisting of: halogen, hydroxy, cyano, $C_{1-4}$alkyl, halo$C_{1-4}$alkyl, $C_{1-4}$alkoxy, halo$C_{1-4}$alkoxy, $C_{1-4}$alkanoyl or $SF_5$; or corresponds to a group $R_5$;

$m_1$, $m_2$, $m_3$, and $m_4$ are 0;

$m_5$, $m_6$ and $m_7$ are each independently 0, 1 or 2 wherein the sum of $m_5$, $m_6$ and $m_7$ is 1 or 2;

$R_6$ is $C_{1-6}$alkyl;

$R_7$ is halogen, $C_{1-6}$alkyl or halo$C_{1-6}$alkyl;

$R_2$ is hydrogen or $C_{1-4}$alkyl;

n is 2 or 3;

X is S or —CH₂—;

R₃ is C₁₋₄alkyl;

R₄ is hydrogen, or a phenyl group, a heterocyclyl group, a 5- or 6-membered heteroaromatic group, or a 8- to 11-membered bicyclic group, any of which groups is optionally substituted by 1, 2, 3 or 4 substituents selected from the group consisting of: halogen, cyano, C₁₋₄alkyl, haloC₁₋₄alkyl, C₁₋₄alkoxy and C₁₋₄alkanoyl;

R₅ is isoxazolyl, —CH₂—N-pyrrolyl, 1,1-dioxido-2-isothiazolidinyl, thienyl, thiazolyl, pyridyl or 2-pyrrolidinonyl, wherein each group is optionally substituted by one or two substituents selected from: halogen, cyano, C₁₋₄alkyl, haloC₁₋₄alkyl, C₁₋₄alkoxy and C₁₋₄alkanoyl; with the proviso that when m5=m6=1, R₇ is not chlorine.

In a further embodiment, the present invention provides a compound of formula (ID) or a salt thereof:

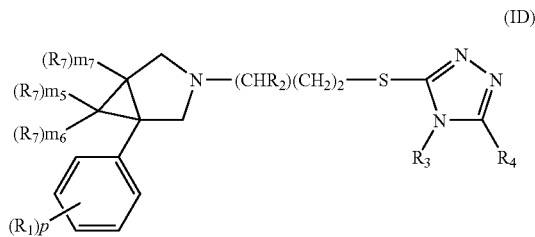

(ID)

wherein p, R₁, m₅, m₆, m₇, R₂, R₃, R₄, R₇ are defined as above for compounds of formula (IC).

The term "5- or 6-membered ring containing one or two heteroatoms independently selected from nitrogen and oxygen" refers to a non-saturated carbocyclic ring wherein one or two of the carbon atoms are replaced by nitrogen and/or oxygen. Examples include furanyl, pyrrolyl, pyrrolinyl, pyrrolidinyl, oxazolyl, imidazolyl, pyrazolidinyl, isoxazolyl, pyranyl, pyridinyl, pyridazinyl, pyrimidinyl and pyrazinyl.

The term "C₁₋₄alkyl" refers to an alkyl group having from one to four carbon atoms, in all isomeric forms, such as methyl, ethyl, propyl, isopropyl, butyl, isobutyl, sec-butyl and tert-butyl. The term "n-C₁₋₄alkyl" refers to the unbranched alkyls as defined above.

The term "C₁₋₄alkoxy" refers to a straight chain or branched chain alkoxy (or "alkyloxy") group having from one to four carbon atoms, such as methoxy, ethoxy, propoxy, isopropoxy, butoxy, isobutoxy, sec-butoxy and tert-butoxy.

The term "C₁₋₄alkanoyl" refers to an alkanoyl group having from 1 to 4 carbon atoms, such as methanoyl (or "formyl"), ethanoyl (or "acetyl"), propanoyl, isopropanoyl, butanoyl, isobutanoyl and sec-butanoyl.

The term "halogen" and its abbreviation "halo" refer to fluorine (F), chlorine (Cl), bromine (Br) or iodine (I). Where the term "halo" is used before another group, it indicates that the group is substituted by one, two or three halogen atoms. For example, "haloC₁₋₄alkyl" refers to groups such as trifluoromethyl, bromoethyl, trifluoropropyl, and other groups derived from C₁₋₄alkyl groups as defined above; and the term "haloC₁₋₄alkoxy" refers to groups such as trifluoromethoxy, bromoethoxy, trifluoropropoxy, and other groups derived from C₁₋₄alkoxy groups as defined above.

The term "5- or 6-membered heteroaromatic group" refers to a monocyclic 5- or 6-membered heterocyclic group containing 1, 2, 3 or 4 heteroatoms, for example from 1 to 3 heteroatoms, selected from O, N and S. When the group contains 2-4 heteroatoms, one may be selected from O, N and S and the remaining heteroatoms may be N. Examples of 5 and 6-membered heteroaromatic groups include pyrrolyl, imidazolyl, pyrazolyl, oxazolyl, isoxazolyl, oxadiazolyl, isothiazolyl, thiazolyl, furyl, thienyl, thiadiazolyl, pyridyl, triazolyl, triazinyl, pyridazinyl, pyrimidinyl and pyrazinyl.

The term "8- to 11-membered bicyclic group" refers to a bicyclic ring system containing a total of 8, 9, 10 or 11 carbon atoms, wherein 1, 2, 3 or 4 or 5 of the carbon atoms are optionally replaced by a heteroatom independently selected from O, S and N. The term includes bicyclic systems wherein both rings are aromatic, as well as bicyclic ring systems wherein one of the rings is partially or fully saturated. Examples of 8- to 11-membered bicyclic groups wherein both rings are aromatic include indenyl, naphthyl and azulenyl. Examples of 8- to 11-membered bicyclic groups having 1, 2, 3, 4 or 5 heteroatoms, in which both rings are aromatic, include: 6H-thieno[2,3-b]pyrrolyl, imidazo[2,1-b][1,3]thiazolyl, imidazo[5,1-b][1,3]thiazolyl, [1,3]thiazolo[3,2-b][1,2,4]triazolyl, indolyl, isoindolyl, indazolyl, benzimidazolyl e.g. benzimidazol-2-yl, benzoxazolyl e.g. benzoxazol-2-yl, benzisoxazolyl, benzothiazolyl, benzisothiazolyl, benzothienyl, benzofuranyl, naphthridinyl, quinolyl, quinoxalinyl, quinazolinyl, cinnolinyl and isoquinolyl. Examples of 8- to 11-membered bicyclic groups having 1, 2, 3, 4 or 5 heteroatoms, in which one of the rings is partially or fully saturated includes dihydrobenzofuranyl, indanyl, tetrahydronaphthyl, indolinyl, isoindolinyl, tetrahydroisoquinolinyl, tetrahydroquinolyl, benzoxazinyl and benzoazepinyl.

The term "heterocyclyl" refers to a 5 or 6-membered monocyclic or 8 to 11-membered bicyclic group wherein 1, 2, 3, 4 or 5 of the carbon atoms are replaced by a heteroatom independently selected from O, S and N and which is partially or fully saturated. Examples of "heterocyclyl" which are fully saturated 5 or 6-membered monocyclic rings include pyrrolidinyl, imidazolidinyl, pyrazolidinyl, isothiazolyl, thiazolyl, tetrahydrofuranyl, dioxolanyl, piperidinyl, piperazinyl, morpholinyl, thiomorpholinyl, tetrahydrothienyl, dioxanyl, tetrahydro-2H-pyranyl and dithianyl. Examples of "heterocyclyl" groups which are partially saturated 5 or 6-membered monocyclic rings include oxazolinyl, isoaxazolinyl, imidazolinyl, pyrazolinyl, 1,2,3,6-tetrahydropyridyl and 3,6-dihydro-2H-pyranyl. Examples of "heterocyclyl" groups which are fully saturated 8 to 11-membered bicyclic rings include decahydroquinolinyl, octahydro-2H-1,4-benzoxazinyl and octahydro-1H-cyclopenta-[b]pyridinyl. Examples of "heterocyclyl" groups which are partially saturated 8 to 11-membered bicyclic rings include 2,3-dihydro-1H-indolyl, 1,2,3,4-tetrahydroquinolinyl, 1,2,3,4-tetrahydroisoquinolinyl and 2,3,4,5-tetrahydro-1H-3-benzazepinyl.

Any of these groups may be attached to the rest of the molecule at any suitable position.

As used herein, the term "salt" refers to any salt of a compound according to the present invention prepared from an inorganic or organic acid or base, quaternary ammonium salts and internally formed salts. Physiologically acceptable salts are particularly suitable for medical applications because of their greater aqueous solubility relative to the parent compounds. Such salts must clearly have a physiologically acceptable anion or cation. Suitably physiologically acceptable salts of the compounds of the present invention include acid addition salts formed with inorganic acids such as hydrochloric, hydrobromic, hydroiodic, phosphoric, metaphosphoric, nitric and sulfuric acids, and with organic acids, such as tartaric, acetic, trifluoroacetic, citric, malic, lactic, fumaric, benzoic, formic, propionic, glycolic, gluconic, maleic, succinic, camphorsulfuric, isothionic, mucic, gentisic, isonicotinic, saccharic, glucuronic, furoic, glutamic, ascorbic, anthranilic, salicylic, phenylacetic, mandelic, embonic (pamoic), methanesulfonic, ethanesulfonic, pantothenic, stearic, sulfinilic, alginic, galacturonic and arylsulfonic, for example benzenesulfonic and p-toluenesulfonic, acids; base addition salts formed with alkali metals and alkaline earth metals and organic bases such as N,N-dibenzylethylenediamine, chloroprocaine, choline, diethanolamine, ethylenediamine, meglumaine (N-methylglucamine), lysine and procaine; and internally formed salts. Salts having a non-physiologically acceptable anion or cation are within the scope of the invention as useful intermediates for the preparation of physiologically acceptable salts and/or for use in non-therapeutic, for example, in vitro, situations.

In one embodiment, p is 1 or 2.
In a further embodiment p is 1.
In another embodiment p is 0.
In one embodiment n is 2.
In one embodiment X is S.
In one embodiment, $R_1$ is halo$C_{1-6}$alkyl (such as $CF_3$).
In one embodiment, $R_6$ is methyl.
In another embodiment, $R_7$ is methyl.
In one embodiment, $m_1$, $m_2$, $m_4$, $m_5$, $m_6$ and $m_7$ are 0, $m_3$ is 1 and $R_6$ is $C_{1-6}$alkyl such as methyl.
In another embodiment, $m_1$, $m_2$, $m_4$, $m_5$, $m_6$ and $m_3$ are 0, $m_7$ is 1 and $R_7$ is $C_{1-6}$alkyl such as methyl.
In still further embodiment, $m_1$, $m_2$, $m_4$, $m_3$, $m_6$ and $m_7$ are 0, $m_5$ is 1 and $R_7$ is $C_{1-6}$alkyl such as methyl.
In one embodiment, $R_2$ is hydrogen.
In one embodiment, $R_5$ is a group selected from: isoxazolyl, 2-pyrrolidinonyl, 1,1-dioxido-2-isothiazolidinyl which is optionally substituted by one or two substituents selected from: halogen, cyano, $C_{1-2}$alkyl (e.g. methyl), halo$C_{1-2}$alkyl (e.g. trifluoromethyl), $C_{1-2}$alkoxy (e.g. methoxy) and $C_{1-3}$alkanoyl (e.g. acetyl). For example, $R_5$ is isoxazolyl, 2-pyrrolidinonyl, —$CH_2$—N-pyrrolyl, 1,1-dioxido-2-isothiazolidinyl, 2-thienyl, 2-pyridyl or 2-thiazolyl.

In one embodiment, $R_4$ is optionally substituted phenyl (e.g. phenyl, 4-trifluoromethyl-phenyl, 3,4-difluorophenyl), an optionally substituted bicyclic group such as quinolinyl (e.g. 2-methylquinoline, 8-fluoro-2-methylquinoline), an optionally substituted pyranyl (e.g. 4-tetrahydro-2H-pyranyl), an optionally substituted pyridinyl (e.g. 3-methyl-2-pyridinyl, 2-methyl-3-pyridinyl, 3-pyridinyl, 2-methyl-6-trifluoromethyl-3-pyridinyl), an optionally substituted pyrazolyl (e.g. 5-chloro-1-methyl-1H-pyrazol-4-yl, 1-methyl-3-trifluoromethyl-1H-pyrazol-4-yl 1,5-dimethyl-1H-pyrazoly-4-yl), an optionally substituted pyrimidyl (e.g. 5-pyrimidinyl), an optionally substituted pyridazinyl (e.g. 4-pyridazinyl), an optionally substituted pyrazinyl (e.g. 5-methyl-2-pyrazinyl), an optionally substituted furanyl (e.g. 3-methyl-2-furanyl, 2,5-dimethyl-3-furanyl), an optionally substituted thienyl (e.g. 5-chloro-2-thienyl), an optionally substituted oxazolyl (e.g. 4-methyl-1,3-oxazol-5-yl, 2-methyl-5-trifluoromethyl-1,3-oxazol-4-yl), an optionally substituted isoxazolyl (e.g. 3-methyl-5-isoxazolyl), an optionally substituted thiazolyl (e.g. 2,4-dimethyl-1,3-thiazol-5-yl), an optionally substituted triazolyl (e.g. 1-methyl-1H-1,2,3-triazol-4-yl).

In another embodiment, $R_4$ is optionally substituted oxazolyl (such as 4-methyl-1,3-oxazol-5-yl, 2-methyl-5-trifluoromethyl-1,3-oxazol-4-yl).

In one embodiment, $R_3$ is methyl.

Certain groups/substituents included in the present invention may be present as isomers. The present invention includes within its scope all such isomers, including racemates, enantiomers, tautomers and mixtures thereof. Certain of the substituted heteroaromatic groups included in compounds of formula (I) may exist in one or more tautomeric forms. The present invention includes within its scope all such tautomeric forms, including mixtures.

It will be appreciated, in common with most biologically active molecules that the level of biological activity may vary between the individual stereoisomers of a given molecule. It is intended that the scope of the invention includes all individual stereoisomers (diastereoisomers and enantiomers) and all mixtures thereof, including but not limited to racemic mixtures, which demonstrate appropriate biological activity with reference to the procedures described herein.

Because of the presence of the fused cyclopropane, compounds of formula (I) are believed to have a "cis" disposition with respect to the group $(R_7)_{m7}$ and the phenyl group (both groups linked to the bicyclic ring system are on the same face of this bicyclic ring system). In another embodiment of the present invention, compounds of formula (I)' are provided which correspond to the compounds of formula (I) wherein the group $(R_7)_{m7}$ and the phenyl group have a "cis" disposition, represented by the bold highlight of the bonds:

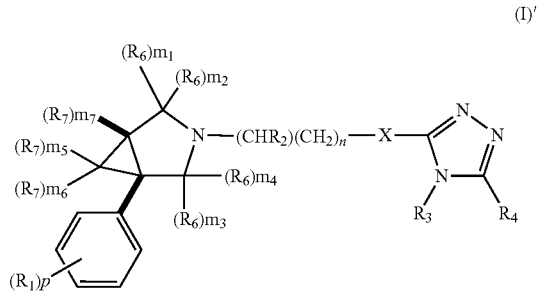

(I)' wherein p, $R_1$, $m_1$, $m_2$, $m_3$, $m_4$, $m_5$, $m_6$, $m_7$, $R_6$, $R_7$, n, X, $R_2$, $R_3$, $R_4$ are defined as above for compounds of formula (I).

The two configurations of compounds of formula (I)' are shown below:

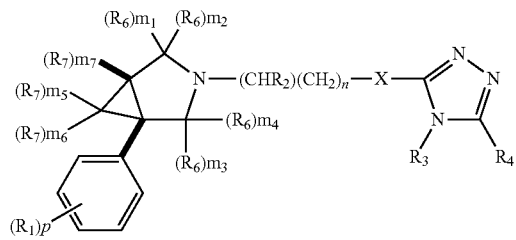

-continued

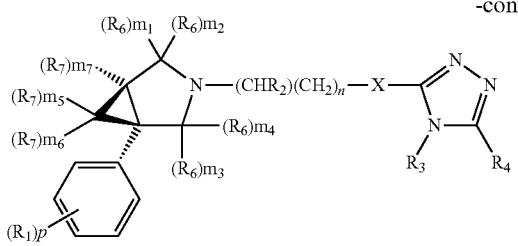

In a further embodiment of the present invention compounds of formula (IA) are provided that correspond to stereochemical isomers of compounds of formula (I)', enriched in one configuration shown below (IA)

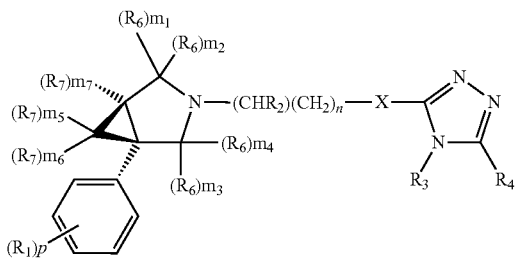

In a further embodiment of the present invention compounds of formula (IB) are provided that correspond to stereochemical isomers of compounds of formula (I)', enriched in one configuration shown below (IB)

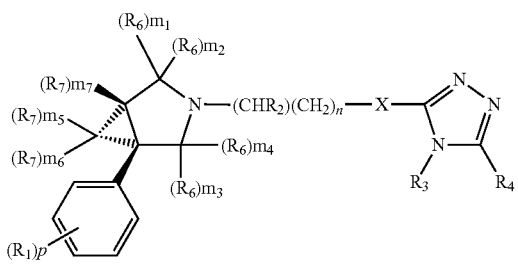

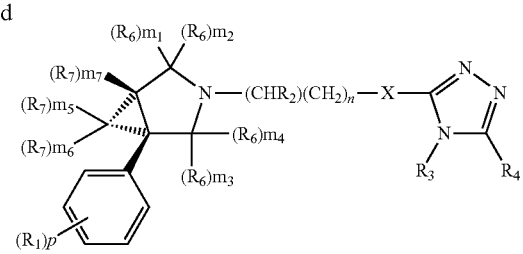

In another embodiment of the present invention, compounds of formula (IC)' are provided which correspond to the compounds of formula (IC) wherein the group $(R_7)_{m7}$ and the phenyl group have a "cis" disposition, represented by the bold highlight of the bonds:

(IC)'

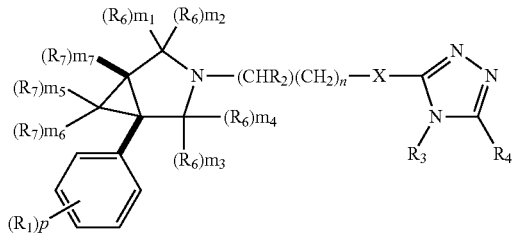

wherein p, $R_1$, $m_1$, $m_2$, $m_3$, $m_4$, $m_5$, $m_6$, $m_7$, $R_6$, $R_7$, n, X, $R_2$, $R_3$, $R_4$ are defined as above for compounds of formula (I).

The two configurations of compounds of formula (IC)' are shown below:

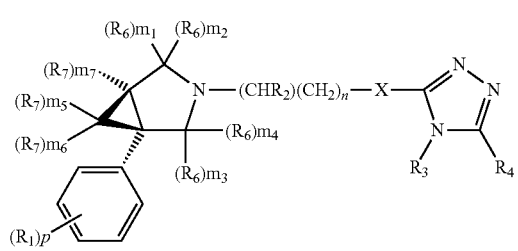

In a further embodiment of the present invention compounds of formula (IE) are provided that correspond to stereochemical isomers of compounds of formula (IC)', enriched in one configuration as shown below:

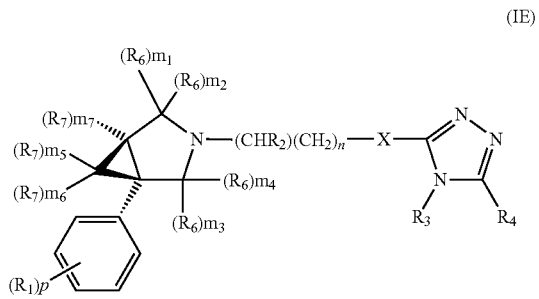

(IE)

In a further embodiment of the present invention compounds of formula (IF) are provided that correspond to stereochemical isomers of compounds of formula (IC)', enriched in one configuration as shown below:

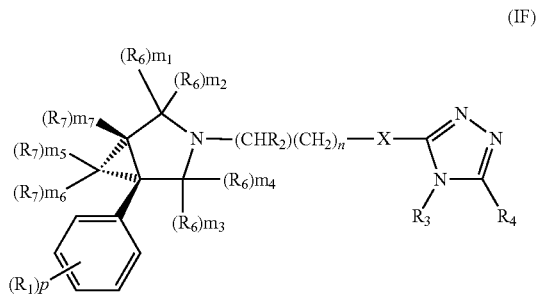

(IF)

It is intended in the context of the present invention that stereochemical isomers enriched in one configuration of formula (IA) or (IE) correspond in one embodiment to at least 90% e.e. In another embodiment the isomers correspond to at least 95% e.e. In another embodiment the isomers correspond to at least 99% e.e.

It is intended in the context of the present invention that stereochemical isomers enriched in one configuration of formula (IB) or (IF) correspond in one embodiment to at least 90% e.e. In another embodiment the isomers correspond to at least 95% e.e. In another embodiment the isomers correspond to at least 99% e.e.

Certain of the compounds of the invention may form acid addition salts with less than one equivalent, or one or more equivalents of the acid. The present invention includes within its scope all possible stoichiometric and non-stoichiometric forms.

Pharmaceutical acceptable salts may also be prepared from other salts, including other pharmaceutically acceptable salts, of the compound of formula (I) using conventional methods.

Those skilled in the art of organic chemistry will appreciate that many organic compounds can form complexes with solvents in which they are reacted or from which they are precipitated or crystallized. These complexes are known as "solvates". For example, a complex with water is known as a "hydrate". Solvates of the compound of the invention are within the scope of the invention. The compounds of formula (I) may readily be isolated in association with solvent molecules by crystallisation or evaporation of an appropriate solvent to give the corresponding solvates.

In addition, prodrugs are also included within the context of this invention. As used herein, the term "prodrug" means a compound which is converted within the body, e.g. by hydrolysis in the blood, into its active form that has medical effects. Pharmaceutically acceptable prodrugs are described in T. Higuchi and V. Stella, Prodrugs as Novel Delivery Systems, Vol. 14 of the A.C.S. Symposium Series, Edward B. Roche, ed., Bioreversible Carriers in Drug Design, American Pharmaceutical Association and Pergamon Press, 1987, and in D. Fleisher, S. Ramon and H. Barbra "Improved oral drug delivery: solubility limitations overcome by the use of prodrugs", Advanced Drug Delivery Reviews (1996) 19(2) 115-130, each of which are incorporated herein by reference.

Prodrugs are any covalently bonded carriers that release a compound of structure (I) in vivo when such prodrug is administered to a patient. Prodrugs are generally prepared by modifying functional groups in a way such that the modification is cleaved, either by routine manipulation or in vivo, yielding the parent compound. Prodrugs include, for example, compounds of this invention wherein hydroxy, amine or sulfhydryl groups are bonded to any group that, when administered to a patient, cleaves to form the hydroxy, amine or sulfhydryl groups. Thus, representative examples of prodrugs include (but are not limited to) acetate, formate and benzoate derivatives of alcohol, sulfhydryl and amine functional groups of the compounds of structure (I). Further, in the case of a carboxylic acid (—COOH), esters may be employed, such as methyl esters, ethyl esters, and the like. Esters may be active in their own right and/or be hydrolysable under in vivo conditions in the human body. Suitable pharmaceutically acceptable in vivo hydrolysable ester groups include those which break down readily in the human body to leave the parent acid or its salt.

Furthermore, some of the crystalline forms of the compounds of structure (I) may exist as polymorphs, which are included in the present invention.

Those skilled in the art will appreciate that in the preparation of the compound of the invention or a solvate thereof it may be necessary and/or desirable to protect one or more sensitive groups in the molecule to prevent undesirable side reactions. Suitable protecting groups for use according to the present invention are well known to those skilled in the art and may be used in a conventional manner. See, for example, "Protective groups in organic synthesis" by T. W. Greene and P. G. M. Wuts (John Wiley & sons 1991) or "Protecting Groups" by P. J. Kocienski (Georg Thieme Verlag 1994). Examples of suitable amino protecting groups include acyl type protecting groups (e.g. formyl, trifluoroacetyl, acetyl), aromatic urethane type protecting groups (e.g. benzyloxycarbonyl (Cbz) and substituted Cbz), aliphatic urethane protecting groups (e.g. 9-fluorenylmethoxycarbonyl (Fmoc), t-butyloxycarbonyl (Boc), isopropyloxycarbonyl, cyclohexyloxycarbonyl) and alkyl type protecting groups (e.g. benzyl, trityl, chlorotrityl). Examples of suitable oxygen protecting groups may include for example alkyl silyl groups, such as trimethylsilyl or tert-butyldimethylsilyl; alkyl ethers such as tetrahydropyranyl or tert-butyl; or esters such as acetate.

When a specific enantiomer of a compound of general formula (I) is required, this may be obtained for example by resolution of a corresponding enantiomeric mixture of a compound of formula (I) using conventional methods. Thus the required enantiomer may be obtained from the racemic compound of formula (I) by use of chiral HPLC procedure.

The subject invention also includes isotopically-labelled compounds, which are identical to those recited in formula (I) and following, but for the fact that one or more atoms are replaced by an atom having an atomic mass or mass number different from the atomic mass or mass number usually found in nature. Examples of isotopes that can be incorporated into compounds of the invention and salts thereof include isotopes of hydrogen, carbon, nitrogen, oxygen, phosphorous, sulphur, fluorine, iodine, and chlorine, such as $^2H$, $^3H$, $^{11}C$, $^{13}C$, $^{14}C$, $^{15}N$ 170, 180, $^{31}P$, $^{32}P$, $^{35}S$, $^{18}F$, $^{36}Cl$, $^{123}I$ and $^{125}I$.

Compounds of the present invention and salts of said compounds that contain the aforementioned isotopes and/or other isotopes of other atoms are within the scope of the present invention. Isotopically-labelled compounds of the present invention, for example those into which radioactive isotopes such as $^3H$, $^{14}C$ are incorporated, are useful in drug and/or substrate tissue distribution assays. Tritiated, i.e., $^3H$, and carbon-14, i.e., $^{14}C$, isotopes are particularly preferred for their ease of preparation and detectability. $^{11}C$ and $^{18}F$ isotopes are particularly useful in PET (positron emission tomography), and $^{125}I$ isotopes are particularly useful in SPECT (single photon emission computerized tomography), all useful in brain imaging. Further, substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances. Isotopically labelled compounds of formula I and following of this invention can generally be prepared by carrying out the procedures disclosed in the Schemes and/or in the Examples below, by substituting a readily available isotopically labelled reagent for a non-isotopically labelled reagent.

In one embodiment of the present invention compounds are provided e a molecular weight of 800 or less. In another embodiment compounds are provided having a molecular weight of 600 or less. Generally, and without being limited thereto, such compounds may have higher oral bioavailability, and sometimes higher solubility and/or brain penetrancy. Molecular weight here refers to that of the unsolvated free base compound, excluding any molecular weight contributed by addition salts, solvent (e.g. water) molecules, prodrug molecular parts cleaved off in vivo, etc.

In general, the compounds or salts of the invention should be interpreted as excluding those compounds (if any) which are so chemically unstable, either per se or in water, that they are clearly unsuitable for pharmaceutical use through all administration routes, whether oral, parenteral or otherwise. Such compounds are known to the skilled chemist. Prodrugs or compounds which are stable ex vivo and which are convertable in the mammalian (e.g. human) body to the inventive compounds are however included.

Example compounds of the present invention include (1R,5S/1S,5R)-1-methyl-3-(3-{[4-methyl-5-(4-methyl-1,3-oxazol-5-yl)-4H-1,2,4-triazol-3-yl]thio}propyl)-5-[4-(trifluoromethyl)phenyl]-3-azabicyclo[3.1.0]hexane and salts thereof.

The present invention also provides a process for preparing a compound of formula (I) or a salt thereof as defined above, which process comprises reacting a compound of formula (II):

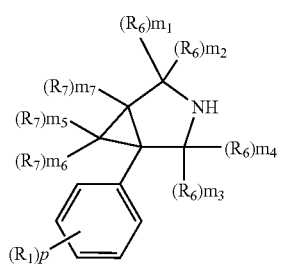

(II)

wherein $R_1$, p and G are as defined for formula (I), with a compound of formula (III):

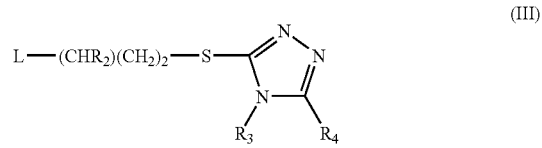

(III)

wherein $R_2$, $R_3$ and $R_4$ are as defined for formula (I) and L is a leaving group, and thereafter optionally:

(i) removing any protecting group(s); and/or (ii) forming a salt; and/or (iii) converting a compound of formula (I) or a salt thereof to another compound of formula (I) or a salt thereof.

The above process may be performed using conventional methods for the formation of a tertiary amine. The leaving group L may be a halogen such as chlorine. Alternatively L may be a sulfonyloxy group such $C_{1-4}$alkylsulfonyloxy (e.g. methanesulfonyloxy), $C_{1-4}$alkylsulfonyloxy or halo$C_{1-4}$alkylsulfonyloxy (e.g. trifluoromethanesulfonyloxy); or arylsulfonyloxy wherein aryl is optionally substituted phenyl, an optionally substituted 5- or 6-membered heteroaromatic group, or an optionally substituted bicyclic group, for example optionally substituted phenyl, wherein in each case the optional substituents are one or more $C_{1-2}$alkyl groups; e.g. para-toluenesulfonyloxy. When L is a halogen the reaction may be carried out using a base such as potassium carbonate in the presence of a source of iodide such as sodium iodide in a solvent such as N,N-dimethylformamide at a suitable temperature, e.g. 60° C.

Compounds of formula (II) may be prepared by methods well known in the art (e.g. *J. Med. Chem.* 1981, 24, 481-490). Interconversion of groups $R_1$ may be effected by methodology well known in the art (e.g. demethylation of a methoxy group resulting in a hydroxy group using a suitable Lewis acidic reagent such as boron tribromide in an inert solvent such as dichloromethane).

One method for preparing a compound of formula (IIa), i.e. compounds of formula (II) wherein $m_1$, $m_2$, $m_3$, $m_5$ and $m_4$ are 0, $m_6$ is 1 and $R_7$ is methyl is shown in scheme 1 below:

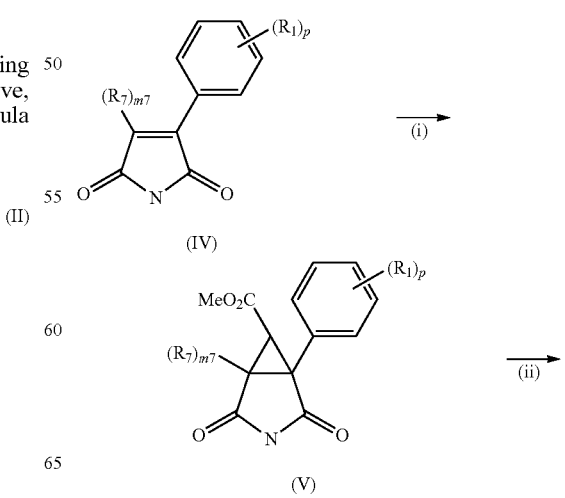

-continued

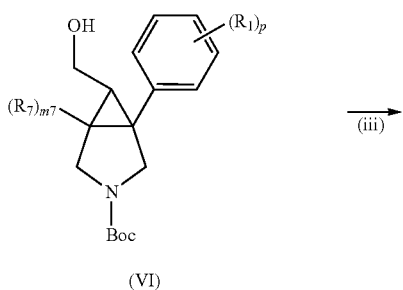

(VI)

(ii) is a direct exhaustive reduction using BH$_3$THF complex in THF, at reflux temperature, for 6-8 hours, followed by usual N-Boc protection with Boc anhydride in DCM. Step (iii) is the oxidation of the primary alcohol to aldehyde, eg. through the standard Swern procedure, then the reduction of the aldehyde to a methyl group (e.g. Synthesis, 2004, 308), followed by Boc removal with TFA in DCM.

In another aspect of the present invention there is provided a synthetic process for the preparation of compounds of formula (IIb), i.e. compounds of general formula (II) wherein $m_1$, $m_2$, $m_3$, $m_5$, $m_6$ and $m_4$ are 0, $m_7$ is 1 and R$_7$ is C$_{1-2}$ alkyl. This process comprises the following steps summarized in Scheme 2:

Scheme 2

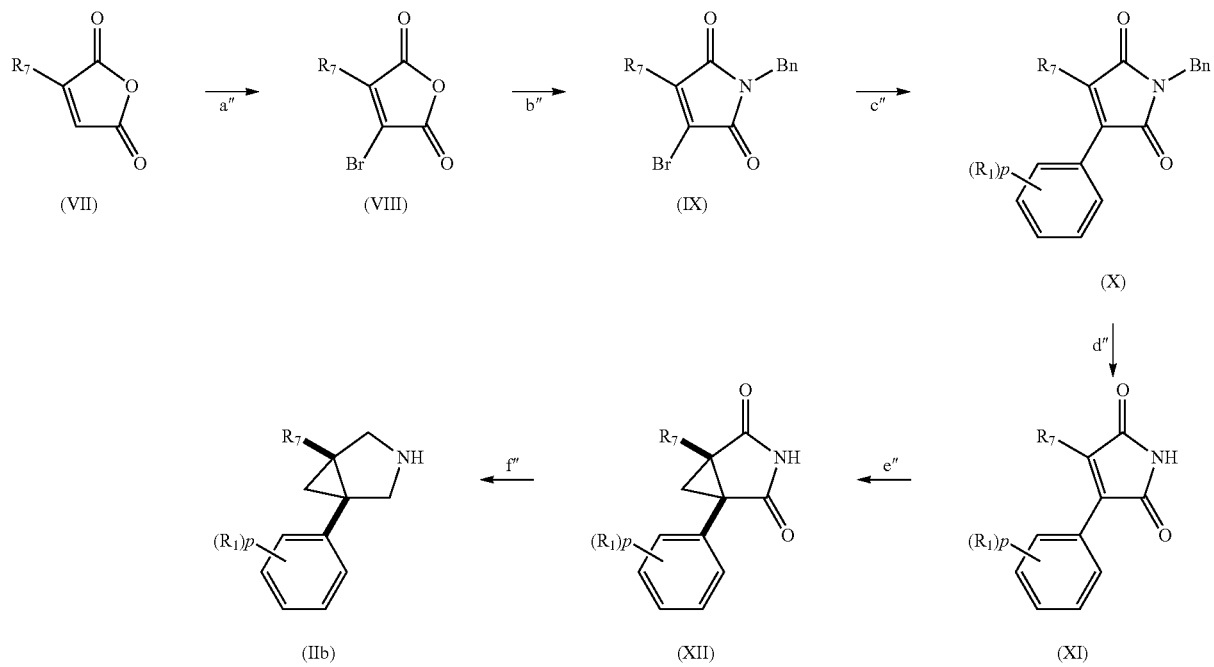

-continued

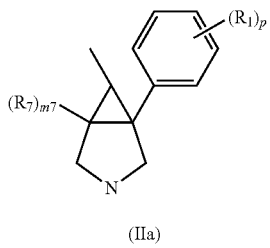

(IIa)

In the above scheme, Step (i) is a cyclopropanation reaction by means of sulphur ylides (e.g. J.O.C., 1999, 64, 547). Step wherein:
step (a″) means bromuration of compound (VII) to give compound (VIII);
step (b″) means reaction of compound (VIII) with a benzylic amine (susceptible to afford benzylic cleavage in acidic conditions) in to give imide (IX);
step (c″) means coupling of compound (IX) with an aryl boronic acid to give compound (X);
step (d″) means removal of the benzylic protecting group of compound (X) to give compound (XI);
step (e″) means cyclopropanation of (XI) to provide bicyclic imide (XII);
step (f″) means reduction of imide (XII) to give compounds of formula (IIb).

Step (a') may be effected using bromine in the presence of AlCl$_3$, and heating the mixture at high temperature, suitably 120° C.

Step (b") may be performed heating compound (VIII) together with an appropriate benzylic amine (suitably 3,4-(dimethoxy)benzylamine or 2,4-(dimethoxy)benzylamine) in the presence of AcONa and AcOH.

Step (c") may be effected using conventional methods for the Suzuki coupling, e.g. using $Pd(PPh_3)_2Cl_2$ as the source of catalytic palladium(0) in the presence of cesium fluoride, $BnEt_3NCl$ and a generic arylboronic acid in an appropriate mixture of solvents, (such as toluene/$H_2O$ 1:1) at a suitable temperature (such as 90° C.).

Step (d") may be performed through an appropriate method for acidic cleavage of benzylic protecting group, such as one of those reported in "Protective groups in organic synthesis" by T. W. Greene and P. G. M. Wuts (John Wiley & sons 1991) or "Protecting Groups" by P. J. Kocienski (Georg Thieme Verlag 1994). Suitably, if the benzylic group is represented by 3,4-(dimethoxy)benzyl, protection may be removed through reaction of compound (X) with TFA and anisole in the presence of sulforic acid.

Step (e") consists of slow addition of a solution of purified compound of formula (XI), or mixtures containing a compound of formula (XI), dissolved in a suitable solvent such as dimethylsulfoxide, to a solution of trimethylsulfoxonium iodide in a suitable solvent such as dimethylsulfoxide and a suitable base, such as sodium hydride. This is followed by allowing time to react as appropriate and a suitable workup.

Step (f") can be performed using a suitable reducing agent in a compatible solvent, such as borane in tetrahydrofuran or Red-Al® in toluene at an appropriate temperature, such as for example 65° C. in the case of borane as the reducing agent. This is followed by a suitable workup.

A compound of formula (III) may itself be prepared by reacting a compound of formula (XIII):

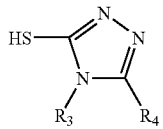

(XIII)

wherein $R_3$ and $R_4$ are as hereinbefore defined; with a compound of formula (XIV):

L(CHR_2)(CH_2)_2Y     (XIV)

wherein $R_2$ is defined as for formula (I) and L and Y are leaving groups, e.g., a bromine or chlorine.

Interconversion reactions between compounds of formula (I) and salts thereof may be performed using methods well known in the art. Examples include:

(i) converting one or more of $R_1$ from alkoxy (e.g. methoxy) to hydroxy, (ii) converting one or more of $R_1$ from hydroxy to sulfonyloxy, such as alkylsulfonyloxy or haloalkylsulfonyloxy, e.g. methanesulfonyloxy or alkylsulfonyloxy or trifluoro-methanesulfonyloxy, (iii) converting one or more of $R_1$ from halogen or perfluoroalkylsulfonyloxy to cyano; and optionally thereafter forming a salt of formula (I).

Compounds of formula (I) have been found to exhibit affinity for dopamine receptors, in particular the $D_3$ receptor, and are expected to be useful in the treatment of disease states which require modulation of such receptors, such as psychotic conditions.

Such affinity is typically calculated from the $IC_{50}$ as the concentration of a compound necessary to displace 50% of the radiolabeled ligand from the receptor, and is reported as a "$K_i$" value calculated by the following equation:

$$K_i = \frac{IC_{50}}{1 + L/K_D}$$

where L=radioligand and $K_D$=affinity of radioligand for receptor (Cheng and Prusoff, *Biochem. Pharmacol.* 22:3099, 1973).

In the context of the present invention pKi (corresponding to the antilogarithm of Ki) is used instead of Ki and the compounds of the present invention typically show pKi greater than 7. In one aspect the present invention provides compounds of formula (I) having a pKi comprised between 7 and 8. In another aspect the present invention provides compounds of formula (I) having a pKi comprised between 8 and 9. In a further aspect the present invention provides compounds of formula (I) having a pKi greater than 9.

Many of the compounds of formula (I) have also been found to have greater affinity for dopamine $D_3$ than for $D_2$ receptors. The therapeutic effect of currently available antipsychotic agents (neuroleptics) is generally believed to be exerted via blockade of $D_2$ receptors; however this mechanism is also thought to be responsible for undesirable extrapyramidal side effects (eps) associated with many neuroleptic agents. It has been suggested that blockade of the recently characterised dopamine $D_3$ receptor may give rise to beneficial antipsychotic activity without significant eps. (see for example Sokoloff et al, Nature, 1990; 347: 146-151; and Schwartz et al, Clinical Neuropharmacology, Vol 16, No. 4, 295-314, 1993). In one embodiment compounds of the present invention are provided which have higher (e.g. ≧10× or ≧100× higher) affinity for dopamine $D_3$ than dopamine $D_2$ receptors (such affinity can be measured using standard methodology for example using cloned dopamine receptors—see herein). Said compounds may suitably be used as selective modulators of $D_3$ receptors.

From the localisation of $D_3$ receptors, it could also be envisaged that the compounds could also have utility for the treatment of a substance-related disorder where it has been suggested that $D_3$ receptors are involved (e.g. see Levant, 1997, Pharmacol. Rev., 49, 231-252). Examples of such substance abuse include alcohol, cocaine, heroin and nicotine abuse. Compounds of formula (I) may be used for treatment of all aspects of drug dependency including drug intake, relapse to drug-seeking behaviour following abstinence and withdrawal symptoms from drugs of abuse such as alcohol, cocaine, opiates, nicotine, benzodiazepines and inhibition of tolerance induced by opioids. In addition, compounds of formula (I) and salts and solvates thereof may be used to reduce craving and therefore will be useful in the treatment of drug craving. Drug craving can be defined as the incentive motivation to self-administer a psychoactive substance that was previously consumed. Three main factors are involved in the development and maintenance of drug craving: (1) Dysphoric states during drug withdrawal can function as a negative reinforcer leading to craving; (2) Environmental stimuli associated with drug effects can become progressively more powerful (sensitization) in controlling drug seeking or craving, and (3) A cognition (memory) of the ability of drugs to promote pleasurable effects and to alleviate a dysphoric state during withdrawal. Craving may account for the difficulty that individuals have in giving up drugs of abuse and therefore contributes significantly to the development and maintenance of drug dependence.

The compounds of formula (I) are of potential use as antipsychotic agents for example in the treatment of schizophrenia, schizo-affective disorders, psychotic depression, mania, paranoid and delusional disorders. Furthermore, they could have utility as adjunct therapy in Parkinsons Disease, particularly with compounds such as L-DOPA and possibly dopaminergic agonists, to reduce the side effects experienced with these treatments on long term use (e.g. see Schwartz et al., Brain Res. Reviews, 1998, 26, 236-242). Other conditions which may be treated by the compounds include dyskinetic disorders such as Parkinson's disease, neuroleptic-induced parkinsonism and tardive dyskinesias; depression; anxiety; cognitive impairment including memory disorders such as Alzheimers disease, eating disorders, sexual dysfunction, sleep disorders, emesis, movement disorders, obsessive-compulsive disorders, amnesia, aggression, autism, vertigo, dementia, circadian rhythm disorders and gastric motility disorders e.g. IBS.

A wide range of psychiatric and neuropsychiatric disorders appear to be related to Obsessive-Compulsive Disorder, and form a family of related disorders referred to as obsessive-compulsive (OC) spectrum disorders. The compounds of formula (I) may be used for the treatment of an obsessive-compulsive spectrum disorder, including somatoform disorders such as body dysmorphic disorder and hyperchondriasis, bulimia nervosa, anorexia nervosa, binge eating, paraphilia and nonparaphilic sexual addictions, Sydeham's chorea, torticollis, autism, compulsive hoarding, and movement disorders, including Tourette's syndrome. As used herein, the phrase "obsessive-compulsive spectrum disorder" is intended to include Obsessive-Compulsive Disorder.

The compounds of formula (I) are also useful for the treatment of premature ejaculation.

Within the context of the present invention, the terms describing the indications used herein are classified in the Diagnostic and Statistical Manual of Mental Disorders, 4th Edition, published by the American Psychiatric Association (DSM-IV) and/or the International Classification of Diseases, 10th Edition (ICD-10). The various subtypes of the disorders mentioned herein are contemplated as part of the present invention. Numbers in brackets after the listed diseases below refer to the classification code in DSM-IV.

Within the context of the present invention, the term "substance-related disorder" includes: —

Substance-related disorders including Substance Use Disorders such as Substance Dependence, Substance Craving and Substance Abuse; Substance-Induced Disorders such as Substance Intoxication, Substance Withdrawal, Substance-Induced Delirium, Substance-Induced Persisting Dementia, Substance-Induced Persisting Amnestic Disorder, Substance-induced Psychotic Disorder, Substance-Induced Mood Disorder, Substance-Induced Anxiety Disorder, Substance-induced Sexual Dysfunction, Substance-Induced Sleep Disorder and Hallucinogen Persisting Perception Disorder (Flashbacks); Alcohol-Related Disorders such as Alcohol Dependence (303.90), Alcohol Abuse (305.00), Alcohol Intoxication (303.00), Alcohol Withdrawal (291.81), Alcohol Intoxication Delirium, Alcohol Withdrawal Delirium, Alcohol-Induced Persisting Dementia, Alcohol-Induced Persisting Amnestic Disorder, Alcohol-Induced Psychotic Disorder, Alcohol-Induced Mood Disorder, Alcohol-induced Anxiety Disorder, Alcohol-Induced Sexual Dysfunction, Alcohol-Induced Sleep Disorder and Alcohol-Related Disorder Not Otherwise Specified (291.9); Amphetamine (or Amphetamine-Like)-Related Disorders such as Amphetamine Dependence (304.40), Amphetamine Abuse (305.70), Amphetamine Intoxication (292.89), Amphetamine Withdrawal (292.0), Amphetamine Intoxication Delirium, Amphetamine Induced Psychotic Disorder, Amphetamine-Induced Mood Disorder, Amphetamine-Induced Anxiety Disorder, Amphetamine-Induced Sexual Dysfunction, Amphetamine-Induced Sleep Disorder and Amphetamine-Related Disorder Not Otherwise Specified (292.9); Caffeine Related Disorders such as Caffeine Intoxication (305.90), Caffeine-Induced Anxiety Disorder, Caffeine-Induced Sleep Disorder and Caffeine-Related Disorder Not Otherwise Specified (292.9); Cannabis-Related Disorders such as Cannabis Dependence (304.30), Cannabis Abuse (305.20), Cannabis Intoxication (292.89), Cannabis Intoxication Delirium, Cannabis-Induced Psychotic Disorder, Cannabis-Induced Anxiety Disorder and Cannabis-Related Disorder Not Otherwise Specified (292.9); Cocaine-Related Disorders such as Cocaine Dependence (304.20), Cocaine Abuse (305.60), Cocaine Intoxication (292.89), Cocaine Withdrawal (292.0), Cocaine Intoxication Delirium, Cocaine-Induced Psychotic Disorder, Cocaine-induced Mood Disorder, Cocaine-Induced Anxiety Disorder, Cocaine-Induced Sexual Dysfunction, Cocaine-Induced Sleep Disorder and Cocaine-Related Disorder Not Otherwise Specified (292.9); Hallucinogen-Related Disorders such as Hallucinogen Dependence (304.50), Hallucinogen Abuse (305.30), Hallucinogen Intoxication (292.89), Hallucinogen Persisting Perception Disorder (Flashbacks) (292.89), Hallucinogen Intoxication Delirium, Hallucinogen-induced Psychotic Disorder, Hallucinogen-Induced Mood Disorder, Hallucinogen-induced Anxiety Disorder and Hallucinogen-Related Disorder Not Otherwise Specified (292.9); Inhalant-Related Disorders such as Inhalant Dependence (304.60), Inhalant Abuse (305.90), Inhalant Intoxication (292.89), Inhalant Intoxication Delirium, Inhalant-induced Persisting Dementia, Inhalant-Induced Psychotic Disorder, Inhalant-Induced Mood Disorder, Inhalant-Induced Anxiety Disorder and Inhalant-Related Disorder Not Otherwise Specified (292.9); Nicotine-Related Disorders such as Nicotine Dependence (305.1), Nicotine Withdrawal (292.0) and Nicotine-Related Disorder Not Otherwise Specified (292.9); Opioid-Related Disorders such as Opioid Dependence (304.00), Opioid Abuse (305.50), Opioid Intoxication (292.89), Opioid Withdrawal (292.0), Opioid Intoxication Delirium, Opioid-Induced Psychotic Disorder, Opioid-Induced Mood Disorder, Opioid-Induced Sexual Dysfunction, Opioid-Induced Sleep Disorder and Opioid-Related Disorder Not Otherwise Specified (292.9); Phencyclidine (or Phencyclidine-Like)-Related Disorders such as Phencyclidine Dependence (304.60), Phencyclidine Abuse (305.90), Phencyclidine Intoxication (292.89), Phencyclidine Intoxication Delirium, Phencyclidine-Induced Psychotic Disorder, Phencyclidine-Induced Mood Disorder, Phencyclidine-Induced Anxiety Disorder and Phencyclidine-Related Disorder Not Otherwise Specified (292.9); Sedative-, Hypnotic-, or Anxiolytic-Related Disorders such as Sedative, Hypnotic, or Anxiolytic Dependence (304.10), Sedative, Hypnotic, or Anxiolytic Abuse (305.40), Sedative, Hypnotic, or Anxiolytic Intoxication (292.89), Sedative, Hypnotic, or Anxiolytic Withdrawal (292.0), Sedative, Hypnotic, or Anxiolytic Intoxication Delirium, Sedative, Hypnotic, or Anxiolytic Withdrawal Delirium, Sedative-, Hypnotic-, or Anxiolytic-Persisting Dementia, Sedative-, Hypnotic-, or Anxiolytic-Persisting Amnestic Disorder, Sedative-, Hypnotic-, or Anxiolytic-Induced Psychotic Disorder, Sedative-, Hypnotic-, or Anxiolytic-Induced Mood Disorder, Sedative-, Hypnotic-, or Anxiolytic-Induced Anxiety Disorder Sedative-, Hypnotic-, or Anxiolytic-Induced Sexual Dysfunction, Sedative-, Hypnotic-, or Anxiolytic-Induced Sleep Disorder and Sedative-, Hypnotic-, or Anxiolytic-Related Disorder Not Otherwise Specified (292.9); Polysubstance-Related Disorder such as Polysubstance Dependence (304.80); and Other (or Unknown)

Substance-Related Disorders such as Anabolic Steroids, Nitrate Inhalants and Nitrous Oxide.

Within the context of the present invention, the term "psychotic disorder" includes: —

Schizophrenia including the subtypes Paranoid Type (295.30), Disorganised Type (295.10), Catatonic Type (295.20), Undifferentiated Type (295.90) and Residual Type (295.60); Schizophreniform Disorder (295.40); Schizoaffective Disorder (295.70) including the subtypes Bipolar Type and Depressive Type; Delusional Disorder (297.1) including the subtypes Erotomanic Type, Grandiose Type, Jealous Type, Persecutory Type, Somatic Type, Mixed Type and Unspecified Type; Brief Psychotic Disorder (298.8); Shared Psychotic Disorder (297.3); Psychotic Disorder Due to a General Medical Condition including the subtypes With Delusions and With Hallucinations; Substance-Induced Psychotic Disorder including the subtypes With Delusions (293.81) and With Hallucinations (293.82); and Psychotic Disorder Not Otherwise Specified (298.9).

In a further aspect therefore the present invention provides a method of treating a condition for which modulation [especially inhibition/antagonism (which may also translate into inverse agonism in constitutively active receptor systems)] of dopamine receptors (especially dopamine $D_3$ receptors) is beneficial, which comprises administering to a mammal (e.g. human) in need thereof an effective amount of a compound of formula (I) or a pharmaceutically (i.e physiologically) acceptable salt thereof. In one embodiment, the condition is a substance-related disorder, a psychotic disorder, an obsessive compulsive spectrum disorder or premature ejaculation.

The invention also provides the use of a compound of formula (I) or a salt thereof in the manufacture of a medicament for the treatment of a condition in a mammal for which modulation [especially inhibition/antagonism (which may also translate into inverse agonism in constitutively active receptor systems)] of dopamine receptors (especially dopamine $D_3$ receptors) is beneficial.

The invention also provides a compound of formula (I) or a salt thereof for use in the treatment of a condition in a mammal for which modulation [especially inhibition/antagonism (which may also translate into inverse agonism in constitutively active receptor systems)] of dopamine receptors (especially dopamine $D_3$ receptors) is beneficial.

In one embodiment, the compounds of the present invention are used in the treatment of a substance-related disorder, a psychotic disorder, an obsessive compulsive spectrum disorder or premature ejaculation.

Thus, a still further aspect the invention provides a method of treating a psychotic disorder (e.g. schizophrenia), a substance-related disorder, an obsessive compulsive spectrum disorder or premature ejaculation, which comprises administering to a mammal (e.g. human) in need thereof an effective amount of a compound of formula (I) as herein defined or a salt thereof.

Also provided is the use of a compound of formula (I) or a salt thereof in the manufacture of a medicament for the treatment of a a psychotic disorder (e.g. schizophrenia), a substance-related disorder, an obsessive compulsive spectrum disorder or premature ejaculation.

Also provided is a compound of formula (I) or a salt thereof for use in the treatment of a psychotic disorder (e.g. schizophrenia), a substance-related disorder, an obsessive compulsive spectrum disorder or premature ejaculation.

Also provided is a compound of formula (I) or a salt thereof for use as a therapeutic substance in a mammal, e.g. for use in the treatment of any of the conditions described herein.

"Treatment" includes prophylaxis, where this is appropriate for the relevant condition(s).

For use in medicine, the compounds of the present invention are usually administered as a standard pharmaceutical composition. The present invention therefore provides in a further aspect a pharmaceutical composition comprising a compound of formula (I) or a pharmaceutically (i.e physiologically) acceptable salt thereof and a pharmaceutically (i.e physiologically) acceptable carrier. The pharmaceutical composition can be for use in the treatment of any of the conditions described herein.

The compounds of formula (I) may be administered by any convenient method, for example by oral, parenteral (e.g. intravenous), buccal, sublingual, nasal, rectal or transdermal administration and the pharmaceutical compositions adapted accordingly.

The compounds of formula (I) and their salts which are active when given orally can be formulated as liquids or solids, for example syrups, suspensions or emulsions, tablets, capsules and lozenges.

A liquid formulation will generally consist of a suspension or solution of the compound or salt in a suitable liquid carrier(s) for example an aqueous solvent such as water, ethanol or glycerine, or a non-aqueous solvent, such as polyethylene glycol or an oil. The formulation may also contain a suspending agent, preservative, flavouring or colouring agent.

A composition in the form of a tablet can be prepared using any suitable pharmaceutical carrier(s) routinely used for preparing solid formulations. Examples of such carriers include magnesium stearate, starch, lactose, sucrose and cellulose.

A composition in the form of a capsule can be prepared using routine encapsulation procedures. For example, pellets containing the active ingredient can be prepared using standard carriers and then filled into a hard gelatin capsule; alternatively, a dispersion or suspension can be prepared using any suitable pharmaceutical carrier(s), for example aqueous gums, celluloses, silicates or oils and the dispersion or suspension then filled into a soft gelatin capsule.

Typical parenteral compositions consist of a solution or suspension of the compound or salt in a sterile aqueous carrier or parenterally acceptable oil, for example polyethylene glycol, polyvinyl pyrrolidone, lecithin, arachis oil or sesame oil. Alternatively, the solution can be lyophilised and then reconstituted with a suitable solvent just prior to administration.

Compositions for nasal administration may conveniently be formulated as aerosols, drops, gels and powders. Aerosol formulations typically comprise a solution or fine suspension of the active substance in a pharmaceutically acceptable aqueous or non-aqueous solvent and are usually presented in single or multidose quantities in sterile form in a sealed container, which can take the form of a cartridge or refill for use with an atomising device. Alternatively the sealed container may be a unitary dispensing device such as a single dose nasal inhaler or an aerosol dispenser fitted with a metering valve which is intended for disposal once the contents of the container have been exhausted. Where the dosage form comprises an aerosol dispenser, it will contain a propellant which can be a compressed gas such as compressed air or an organic propellant such as a fluoro-chlorohydrocarbon. The aerosol dosage forms can also take the form of a pump-atomiser.

Compositions suitable for buccal or sublingual administration include tablets, lozenges and pastilles, wherein the active ingredient is formulated with a carrier such as sugar and acacia, tragacanth, or gelatin and glycerin.

Compositions for rectal administration are conveniently in the form of suppositories containing a conventional suppository base such as cocoa butter.

Compositions suitable for transdermal administration include ointments, gels and patches.

In one embodiment, the composition is in unit dose form such as a tablet, capsule or ampoule.

Each dosage unit for oral administration contains for example from 1 to 250 mg (and for parenteral administration contains for example from 0.1 to 25 mg) of a compound of the formula (I) or a salt thereof calculated as the free base.

The pharmaceutically acceptable compounds of the invention will normally be administered in a daily dosage regimen (for an adult patient) of, for example, an oral dose of between 1 mg and 500 mg, for example between 10 mg and 400 mg, e.g. between 10 and 250 mg or an intravenous, subcutaneous, or intramuscular dose of between 0.1 mg and 100 mg, for example between 0.1 mg and 50 mg, e.g. between 1 and 25 mg of the compound of the formula (I) or a salt thereof calculated as the free base, the compound being administered 1 to 4 times per day. Suitably the compounds will be administered for a period of continuous therapy, for example for a week or more.

Biological Test Methods

Functional potency and intrinsic activity of compounds of this invention can be measured by the following GTPγS scintillation proximity assay (GTPγS-SPA). Cells used in the study are Chinese Hamster Ovary (CHO) Cells.

Cell Line

CHO_D2

CHO_D3

Compounds may be tested according to two alternative protocols:

a) Cell membranes are prepared as follows. Cell pellets are resuspended in 10 volumes of 50 mM HEPES, 1 mM EDTA pH 7.4, using KOH. On the day the following proteases are added to the buffer just prior to giving the homogenisation buffer.

$2.12 \times 10^{-6}$ M Leupeptin (Sigma L2884)–5000× stock=5 mg/ml in buffer 25 ug/ml Bacitracin (Sigma B0125)–1000× stock=25 mg/ml in buffer 1 mM PMSF–100× stock=17 mg/ml in 100% ethanol $2 \times 10^{-6}$M Pepstatin A–1000× stock=2 mM in 100% DMSO The cells are homogenised by 2×15 second bursts in a 1 litre Glass Waring blender in a class two biohazard cabinet. The resulting suspension is spun at 500 g for 20 mins (Beckman T21 centrifuge: 1550 rpm). The supernatant is withdrawn with a 25 ml pipette, aliquotted into pre-chilled centrifuge tubes and spun at 48,000 g to pellet membrane fragments (Beckman T1270: 23,000 rpm for 30 mins). The final 48,000 g pellet is resuspended in Homogenisation Buffer, (4× the volume of the original cell pellet). The 48,000 g pellet is resuspended by vortexing for 5 seconds and homogenized in a dounce homogenizer 10-15 stokes. The prep is distributed into appropriate sized aliquots, (200-1000 ul), in polypropylene tubes and store at −80° C. Protein content in the membrane preparations is evaluated with the Bradford protein assay.

The final top concentration of test drug is 3 uM in the assay and 11 points serial dilution curves 1:4 in 100% DMSO are carried out using a Biomek FX. The test drug at 1% total assay volume (TAV) is added to a solid, white, 384 well assay plate. 50% TAV of precoupled (for 90 mins at 4° C.) membranes, 5 µg/well, and Wheatgerm Agglutinin Polystyrene Scintillation Proximity Assay beads (RPNQ0260, Amersham), 0.25 mg/well, in 20 mM HEPES pH 7.4, 100 mM NaCl, 10 mM $MgCl_2$, 60 µg/ml saponin and 30 µM GDP is added. The third addition was a 20% TAV addition of either buffer, (agonist format) or $EC_{80}$ final assay concentration of agonist, Quinelorane, prepared in assay buffer (antagonist format). The assay was started by the addition of 29% TAV of GTPγ[$^{35}$S] 0.38 nM final (37 MBq/ml, 1160Ci/mmol, Amersham). After all additions assay plates are spun down for 1 min at 1,000 rpm. Assay plates are counted on a Viewlux, 613/55 filter, for 5 min., between 2-6 hours after the final addition.

The effect of the test drug over the basal generates $EC_{50}$ value by an iterative least squares curve fitting programme, expressed in the table as $pEC_{50}$ (i.e. $-logEC_{50}$). The ratio between the maximal effect of the test drug and the maximal effect of full agonist, Quinelorane, generates the Intrinsic Activity (IA) value (i.e. IA=1 full agonist, IA<1 partial agonist). fpKi values of test drug are calculated from the $IC_{50}$ generated by "antagonist format" experiment, using Cheng & Prusoff equation: $fKi=IC_{50}/1+([A]/EC_{50})$ where: [A] is the concentration of the agonist 5-HT in the assay and $EC_{50}$ is the 5-HT $EC_{50}$ value obtained in the same experiment. fpKi is defined as $-logfKi$.

b) Cell membranes are prepared as follows. Cell pellets are resuspended in 10 volumes of 50 mM HEPES, 1 mM EDTA pH 7.4, using KOH. On the day the following proteases are added to the buffer just prior to giving the homogenisation buffer.

$10^{-4}$ M Leupeptin (Sigma L2884)

25 ug/ml Bacitracin (Sigma B0125)

1 mM PMSF–100× stock=17 mg/ml in 100% ethanol $2 \times 10^{-6}$M Pepstatin A–500× stock=1 mM in 100% ethanol The cells were homgenised within a glass waring blender for 2×15 secs in 200 mls of 50 mM HEPES+10−4M leupeptin+25 ug/ml bacitracin+1 mM EDTA+1 mM PMSF+2 uM Pepstatin A, (the latter 2 reagents added as fresh ×100 and ×500 stocks respectively in ethanol). The blender was plunged into ice for 5 mins after the first burst and 10-40 mins after the final burst to allow foam to dissipate. The material was then spun at 500 g for 20 mins and the supernatant spun for 36 mins at 48,000 g. The pellet was resuspended in the same buffer as above but without PMSF and Pepstatin A. The material was then forced through a 0.6 mm needle, made up to the required volume, (usually ×4 the volume of the original cell pellet), aliquoted and stored frozen at −80 deg C.

The final top concentration of test drug is 3 uM in the assay and 11 points serial dilution curves 1:4 in 100% DMSO are carried out using a Biomek FX. The test drug at 1% total assay volume (TAV) is added to a solid, white, 384 well assay plate. 50% TAV of precoupled (for 60 mins at RT) membranes, 5 µg/well, and Wheatgerm Agglutinin Polystyrene Scintillation Proximity Assay beads (RPNQ0260, Amersham), 0.25 mg/well, in 20 mM HEPES pH 7.4, 100 mM NaCl, 10 mM $MgCl_2$, 60 µg/ml saponin and 30 µM GDP is added. The third addition was a 20% TAV addition of either buffer, (agonist format) or EC80 final assay concentration of agonist, Quinelorane, prepared in assay buffer (antagonist format). The assay was started by the addition of 29% TAV of GTP

[35S] 0.38 nM final (37 MBq/ml, 1160Ci/mmol, Amersham). After all additions assay plates are spun down for 1 min at 1,000 rpm. Assay plates are counted on a Viewlux, 613/55 filter, for 5 min., between 3-6 hours after the final addition.

The effect of the test drug over the basal generates EC50 value by an iterative least squares curve fitting programme, expressed in the table as pEC50 (i.e. −logEC50). The ratio between the maximal effect of the test drug and the maximal effect of full agonist, Quinelorane, generates the Intrinsic Activity (IA) value (i.e. IA=1 full agonist, IA<1 partial agonist). fpKi values of test drug are calculated from the $IC_{50}$ generated by "antagonist format" experiment, using Cheng & Prusoff equation: fKi=IC50/1+([A]/EC50) where: [A] is the concentration of the agonist Quinelorane in the assay and EC50 is the Quinelorane EC50 value obtained in the same experiment. fpKi is defined as −logfKi.

The compounds of the invention listed above have pKi values within the range of 7.0-10.5 at the dopamine D3 receptor. pKi results are only estimated to be accurate to about ±0.3-0.5.

The compounds of the invention listed above have a selectivity over D2 greater than 30.

EXAMPLES

The invention is further illustrated by the following non-limiting examples.

All temperatures refer to ° C. Infrared spectra were measured on a FT-IR instrument. Compounds were analysed by direct infusion of the sample dissolved in acetonitrile into a mass spectra operated in positive electro spray (ES+) ionisation mode. Proton Magnetic Resonance ($^1$H-NMR) spectra were recorded at 400 MHz, chemical shifts are reported in ppm downfield (d) from $Me_4Si$, used as internal standard, and are assigned as singlets (s), broad singlets (bs), doublets (d), doublets of doublets (dd), triplets (t), quartets (q) or multiplets (m).

Column chromatography was carried out over silica gel (Merck AG Darmstaadt, Germany). The following abbreviations are used in the text: HOBt=1-hydroxybenzotriazole EtOAc=ethyl acetate, $Et_2O$=dietyl ether, DMF=N,N'-dimethylformamide, MeOH=methanol, SCX=strong cation exchanger, Tlc refers to thin layer chromatography on silica plates, and dried refers to a solution dried over anhydrous sodium sulphate, r.t. (RT) refers to room temperature, Rt=retention time, DMSO=dimethyl sulfoxide; DCM=dichloromethane; AcOH=acetic acid; AcONa=sodium acetate; AcOEt=ethyl acetate.

Preparation 1: 3-bromo-4-methyl-2,5-furandione (P1)

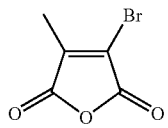

A mixture of 3-methyl-2,5-furandione (citraconic anhydride, 1 g), $AlBr_3$ (26 mg) and $Br_2$ (0.46 mL) was heated at 120° C. overnight. Ethyl acetate was then added and the organic phase was washed with HCl 0.1% and then with brine. The organic phase was dried and concentrated in vacuo to give the crude product (1.680 g) that was used without further purification.

NMR ($^1$H, $CDCl_3$): δ 2.18 (s, 3H)

Preparation 2: 11-{[3,4-bis(methyloxy)phenyl]methyl}-3-bromo-4-methyl-1H-pyrrole-2,5-dione (P2)

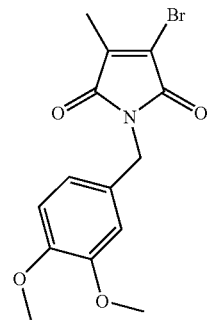

A mixture of 3-bromo-4-methyl-2,5-furandione (P1, 1 g), 1-[3,4-bis(methyloxy)phenyl]methanamine (874 mg), and AcOH (20 mL) was heated at 100° C. overnight. The solution was then concentrated in vacuo. AcOH (20 mL) and AcONa (315 mg) were added to the crude product and the mixture was refluxed for 2 hours. Water was then added and the aqueous phase was extracted with DMC. The organic phase was dried and evaporated in vacuo. The crude product was purified by flash chromatography eluting with cyclohexane/AcOEt from 9/1 to 8/2 to give the title compound (1.364 g).

NMR ($^1$H, $CDCl_3$) δ 7.75 (dd, 4H), 7.03 (m, 2H), 6.80 (d, 1H), 4.70 (s, 2H), 3.89 (s, 3H), 3.87 (s, 3H), 2.25 (s, 3H).

Preparation 3: 1-{[3,4-bis(methyloxy)phenyl]methyl}-3-methyl-4-[4-(trifluoromethyl)phenyl]-1H-pyrrole-2,5-dione (P3)

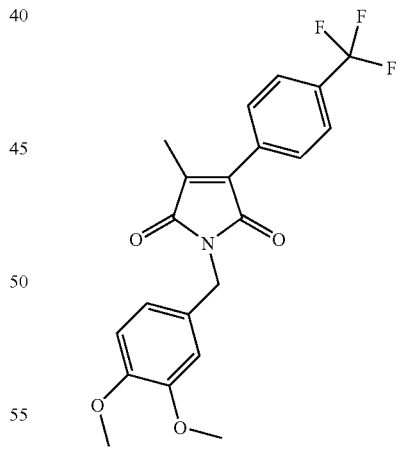

A solution of 11-{[3,4-bis(methyloxy)phenyl]methyl}-3-bromo-4-methyl-1H-pyrrole-2,5-dione (P2, 1 g), [4-(trifluoromethyl)phenyl]boronic acid (1.117 g), $Pd(PPh_3)_2Cl_2$ (206 mg), cesium fluoride (1.206 g) and benzyltriethylammonium chloride (67 mg), in toluene/$H_2O$ 1:1 (30 mL) was heated at 90° C. overnight. The solution was then concentrated in vacuo, dichloromethane was added and the organic phase washed with $NH_4Cl$ (aqueous saturated solution), dried on sodium sulphate and evaporated in vacuo. The crude product was purified by flash chromatography eluting with cyclohexane/ethyl acetate from 7/3 to 4/6 to give the title compound (1.183 g).

NMR ($^1$H, CDCl$_3$) δ 7.75 (dd, 4H), 7.05 (m, 2H), 6.80 (d, 1H), 4.69 (s, 2H), 3.89 (s, 3H), 3.87 (s, 3H), 2.25 (s, 3H).

Preparation 4: 3-methyl-4-[4-(trifluoromethyl)phenyl]-1H-pyrrole-2,5-dione (P4)

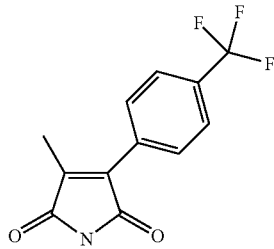

A solution of 1-{[3,4-bis(methyloxy)phenyl]methyl}-3-methyl-4-[4-(trifluoromethyl)phenyl]-1H-pyrrole-2,5-dione (P3, 100 mg), anisole (107 μL), TFA (4 mL) and H$_2$SO$_4$ (catalytic amount) was heated at 90° C. overnight. The solution was then concentrated in vacuo, dichloromethane was added and the organic phase was washed with NaHCO$_3$ (aqueous saturated solution), dried on sodium sulphate and evaporated in vacuo. The crude was purified by flash chromatography eluting with cyclohexane/ethyl acetate 8/2 to give the title compound (50 mg).

NMR (1H, CDCl$_3$) δ 7.78 (dd, 4H), 7.35 (bs, 1H), 2.25 (s, 3H). MS (m/z): 254[M]$^-$

Preparation 5: (1R,5S/1S,5R)-1-methyl-5-[4-(trifluoromethyl)phenyl]-3-azabicyclo[3.1.0]hexane-2,4-dione (P5)

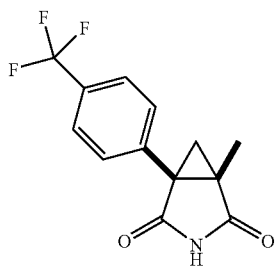

Sodium hydride 60% (15 mg) was added in small portions to a stirred solution of trimethylsulfoxonium iodide (83 mg) in DMSO (anhydrous, 1 ml) and the resulting mixture was allowed to stir at room temperature for 1.5 h. 3-Methyl-4-[4-(trifluoromethyl)phenyl]-1H-pyrrole-2,5-dione (P4, 48 mg) dissolved in DMSO (anhydrous, 1 ml) was then added dropwise and the resulting mixture was allowed to stir at room temperature for 20 minutes. Temperature was then reduced to 0° C. and NH$_4$Cl (aqueous saturated solution) was slowly added, followed by Et$_2$O. After separation of the two phases, the aqueous layer was repeatedly extracted with Et$_2$O. Combined organic layers were washed with brine and then dried over Na$_2$SO$_4$ and evaporated in vacuo. The crude was purified by flash chromatography eluting with cyclohexane/ethyl acetate from 8/2 to 7/3 to give the title compound (28 mg).

NMR ($^1$H, CDCl$_3$) δ 7.7 (d, 2H), 7.48 (m, 3H), 2.15 (d, 1H), 1.85 (d, 1H), 1.25 (s, 3H). MS (m/z): 268[M]$^-$

Preparation 6: (1R,5S/1S,5R)-1-methyl-5-[4-(trifluoromethyl)phenyl]-3-azabicyclo[3.1.0]hexane (P6)

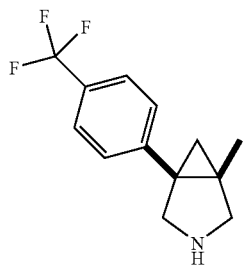

To a solution of borane (1M in tetrahydrofuran, 208 μl) was added (1R,5S/1S,5R)-1-methyl-5-[4-(trifluoromethyl)phenyl]-3-azabicyclo[3.1.0]hexane-2,4-dione (P5, 28 mg) dissolved in tetrahydrofuran (anhydrous, 1 mL) and then the solution was reflux for 6 hours. The mixture was cooled to 0° C. and aqueous hydrochloric acid (6 M, 0.5 mL) was cautiously added monitoring gas evolution and then the mixture was reflux for 3 h. Sodium hydroxide (5 M solution) was added until pH 5 had been reached. The aqueous layer was extracted with DCM. The organic phase was dried and evaporated in vacuo. The residue was charged onto an SCX column and eluted with MeOH followed by MeOH/NH$_3$ 0.25 M. The methanole/ammonia fractions were concentrated under reduced pressure to give of the title compound (15 mg).

NMR ($^1$H, CDCl$_3$) δ 7.58 (d, 2H), 7.39 (d, 2H), 3.27 (bs, 2H), 3.15 (d, 1H), 3.01 (d, 1H), 0.99 (m, 4H), 0.92 (d, 1H). MS (m/z): 242.2 [MH]$^+$.

Preparation 7: 3-[(3-chloropropyl)thio]-4-methyl-5-(4-methyl-1,3-oxazol-5-yl)-4H-1,2,4-triazole (P7)

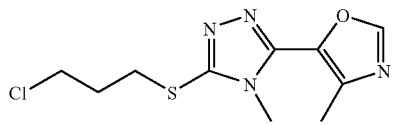

Ethyl-2-chloroacetoacetate (1 wt; 1 eq., 1000 g) was aged with formamide (0.68 vol; ca. 2.8 eq.) and the resulting solution was heated to 120° C. After 5 hours the mixture was allowed to cool to room temperature and allowed to age under nitrogen over night. The mixture was treated with NaOH (3 M, 6 vol, reaction moderately exothermic) and stirred at room temperature for 4 hours. Ethyl acetate (6 vol) was added and the phases allowed to separate. The organic layer was discarded while the aqueous was acidified with conc. (32%) aqueous HCl to pH 2 (ca. 2.0 vol). A precipitate started to form. The suspension was treated with AcOEt (8 vol) and vigorously stirred until the bulk of the precipitate had dissolved. The aqueous phase was further extracted with AcOEt twice (6 vol each) and the combined organic layers distilled to low volume (again a suspension was observed at low volume). Fresh AcOEt (8 vol) was added and the mixture evaporated to dryness. The collected solid was placed in the oven at 40° C. over night under reduced pressure to give 4-methyl-1, 3-oxazole-5-carboxylic acid (498 g, 64.5%).

This material (498 g, 1 wt) was dissolved in dry tetrahydrofuran (5 vol), under nitrogen, cooled to 0° C. DCC (1.62 wt, 1 eq) was added portionwise followed by HOBt (1.07 wt, 1 eq). The mixture was warmed to 25±2° C. and stirred for 30 min. 4-Methyl-3-thiosemicarbazide (0.83 wt, 1 eq) was then added and the mixture further stirred for 2 h at 25±2° C. The mixture was filtered and the cake was washed with fresh tetrahydrofuran (1 vol) and dried on the filter for a few hours. The cake was suspended in 1 M aqueous NaOH (13 vol) and heated to 70° C. for 30 min. After this time, the mixture was cooled to 25±2° C. and a solid was removed by filtration. The cake was washed with 1 M aqueous NaOH (10 vol). The combined mother liquors were cooled to 0° C. and acidified to ca. pH with HCl (aqueous, 16%; NOTE: keep temperature while adding HCl below +10° C.). The suspended product was isolated by filtration washing with water (2×3 vol). The cake was dried at 40° C. for 18 h in high vacuum to obtain 4-methyl-5-(4-methyl-1,3-oxazol-5-yl)-2,4-dihydro-3H-1,2,4-triazole-3-thione (respectively a tautomeric form thereof; 290 g, 37%).

NaOEt (21% solution in EtOH, 2.08 vol, 1.1 eq) was added to EtOH (20 vol) under nitrogen atmosphere. 4-Methyl-5-(4-methyl-1,3-oxazol-5-yl)-2,4-dihydro-3H-1,2,4-triazole-3-thione (respectively a tautomeric form thereof; 290 g, 1 wt) was added in one portion and the resulting mixture stirred at 25±2° C. until a clear solution was obtained. Then 1-bromo-3-chloropropane (0.54 vol, 1.1 eq) was added and the solution stirred at 40° C. for 24 h then cooled to 25° C. After filtration water (20 vol) was added and the ethanolic phase was removed by vacuum distillation (internal temperature ~40° C.). The mixture was extracted with EtOAc (41 vol). The aqueous layer was removed and the organic phase was evaporated to dryness. Dichloromethane (4 vol) was added. The organic solution is purified through a short silica gel column (18 wt of silica), eluting with EtOAc (200 vol) to give the title compound as a foam (267.64 g).

NMR ($^1$H, CDCl$_3$): δ 7.90 (s, 1H), 3.70 (s, 5H), 3.40 (t, 2H), 2.52 (s, 3H), 2.30 (m, 2H).

Example 1

(1R,5S/1S,5R)-1-methyl-3-(3-{[4-methyl-5-(4-methyl-1,3-oxazol-5-yl)-4H-1,2,4-triazol-3-yl]thio}propyl)-5-[4-(trifluoromethyl)phenyl]-3-azabicyclo[3.1.0]hexane hydrochloride

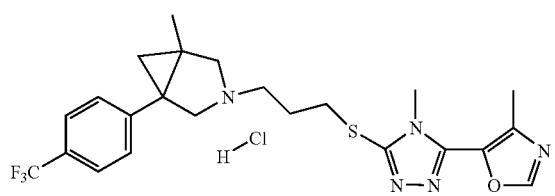

A mixture of (1R,5S/1S,5R)-1-methyl-5-[4-(trifluoromethyl)phenyl]-3-azabicyclo[3.1.0]hexane (P6, 13 mg), 3-[(3-chloropropyl)thio]-4-methyl-5-(4-methyl-1,3-oxazol-5-yl)-4H-1,2,4-triazole (P7, 29 mg), K$_2$CO$_3$ (9 mg) and NaI (10 mg) in DMF (0.5 mL) was heated at 60° C. for 24 h. DCM was added to the reaction mixture and the organic layer was washed with saturated aqueous solution of NH$_4$Cl, dried over Na$_2$SO$_4$ and the solvent evaporated under reduced pressure. The crude product was purified by flash chromatography (eluting with cychloexane/ethyl acetate from 3/7 to 2/8) to give 7 mg of the free base of the title compound. To a solution of this material in dichloromethane HCl (1M in Et$_2$O, 15 μL) was added, the solvent evaporated under vacuum to give 4 mg of the title compound as a white slightly hygroscopic solid.

NMR ($^1$H, CDCl$_3$): 7.95 (m, 1H), 7.57 (d, 2H), 7.39 (d, 2H), 3.73 (m, 3H), 3.36 (m, 2H), 3.23 (m, 2H), 2.69 (m, 3H), 2.55 (m, 3H), 2.41 (m, 1H), 2.02 (m, 2H), 1.51 (m, 1H), 0.97 (m, 3H), 0.78 (m, 1H). MS (m/z): 478.23 [MH]$^+$.

All publications, including but not limited to patents and patent applications, cited in this specification are herein incorporated by reference as if each individual publication were specifically and individually indicated to be incorporated by reference herein as though fully set forth.

The application of which this description and claims forms part may be used as a basis for priority in respect of any subsequent application. The claims of such subsequent application may be directed to any feature or combination of features described herein. They may take the form of product, composition, process, or use claims and may include, by way of example and without limitation, the following claims:

The invention claimed is:

1. A compound of formula (IC) or a salt thereof:

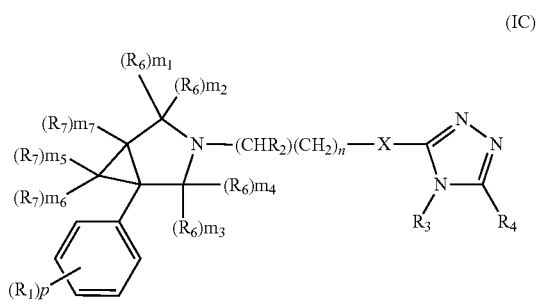

wherein:

p is 0 to 4;

R$_1$ is independently selected from a group consisting of: halogen, hydroxy, cyano, C$_{1-4}$alkyl, haloC$_{1-4}$alkyl, C$_{1-4}$alkoxy, haloC$_{1-4}$alkoxy, and C$_{1-4}$alkanoyl or SF$_5$; or is R$_5$;

m$_1$, m$_2$, m$_3$, and m$_4$ are 1;

m$_5$, m$_6$ and m$_7$ are each independently 0, 1 or 2 wherein the sum of m$_5$, m$_6$ and m$_7$ is 1 or 2;

R$_6$ is C$_{1-6}$alkyl;

R$_7$ is halogen, C$_{1-6}$alkyl or haloC$_{1-6}$alkyl;

R$_2$ is hydrogen or C$_{1-4}$alkyl;

n is 2 or 3;

X is S;

R$_3$ is C$_{1-4}$alkyl;

R$_4$ is hydrogen, phenyl, a heterocyclyl group, a 5- or 6-membered heteroaromatic group, or a 8- to 11-membered bicyclic group, any of which groups is optionally substituted by 1, 2, 3 or 4 substituents selected from the group consisting of halogen, cyano, C$_{1-4}$alkyl, haloC$_{1-4}$alkyl, C$_{1-4}$alkoxy and C$_{1-4}$alkanoyl;

R$_5$ is isoxazolyl, —CH$_2$—N-pyrrolyl, 1,1-dioxido-2-isothiazolidinyl, thienyl, thiazolyl, pyridyl or 2-pyrrolidinonyl, wherein each group is optionally substituted by one or two substituents selected from the group consisting of halogen, cyano, C$_{1-4}$alkyl, haloC$_{1-4}$alkyl, C$_{1-4}$alkoxy and C$_{1-4}$alkanoyl;

with the proviso that when m$_5$=m$_6$=1, R$_7$ is not chlorine.

2. A compound as claimed in claim 1, wherein p is 1 or 2.

3. A compound as claimed in claim 1, wherein $R_1$ is haloC$_{1-6}$alkyl.

4. A compound as claimed claim 1, wherein $R_7$ is methyl.

5. A compound as claimed in claim 1, wherein $m_1$, $m_2$, $m_4$, $m_5$, $m_6$ and $m_3$ are 0, $m_7$ is 1 and $R_7$ is $C_{1-6}$alkyl.

6. A compound as claimed in claim 1, wherein $m_1$, $m_2$, $m_4$, $m_3$, $m_6$ and $m_7$ are 0, $m_5$ is 1 and $R_7$ is $C_{1-6}$alkyl.

7. A compound as claimed in claim 1, wherein $R_2$ is hydrogen.

8. A compound as claimed in claim 1, wherein $R_4$ is optionally substituted oxazolyl.

9. A compound as claimed in claim 1, wherein $R_3$ is methyl.

10. A compound as claimed in claim 1, which is (1R,5S/1S,5R)-1-methyl-3-(3-{[4-methyl-5-(4-methyl-1,3-oxazol-5-yl)-4H-1,2,4-triazol-3-yl]thio}propyl)-5-[4-(trifluoromethyl)phenyl]-3-azabicyclo[3.1.0]hexane or a salt thereof.

11. A compound as claimed in claim 1, having a formula (IC)' or a salt thereof:

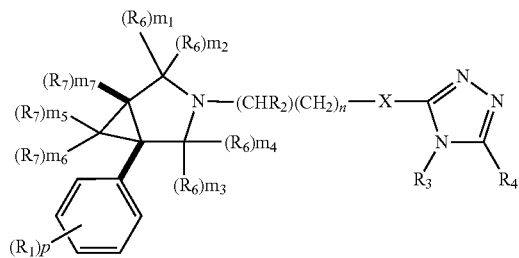

wherein p, $R_1$, $m_1$, $m_2$, $m_3$, $m_4$, $m_5$, $m_6$, $m_7$, $R_6$, $R_7$, n, X, $R_2$, $R_3$, $R_4$ are defined in claim 1.

12. A pharmaceutical composition comprising a compound as claimed in claim 1, or a pharmaceutically acceptable salt thereof, and a pharmaceutically acceptable carrier.

* * * * *